United States Patent [19]

Effenberger et al.

[11] Patent Number: 4,568,781
[45] Date of Patent: Feb. 4, 1986

[54] PREPARATION OF FLUORINE-SUBSTITUTED AROMATIC COMPOUNDS

[75] Inventors: Franz Effenberger, Stuttgart; Willi Streicher, Aalen, both of Fed. Rep. of Germany

[73] Assignee: BASF Aktiengesellschaft, Fed. Rep. of Germany

[21] Appl. No.: 689,248

[22] Filed: Jan. 7, 1985

[30] Foreign Application Priority Data

Jan. 7, 1984 [DE] Fed. Rep. of Germany ....... 3400418

[51] Int. Cl.$^4$ ...................... C07C 79/10; C07C 79/12
[52] U.S. Cl. .................................. 568/937; 260/694; 568/933; 568/938
[58] Field of Search ...................... 568/937, 938, 933; 260/694

[56] References Cited

U.S. PATENT DOCUMENTS

| | | | |
|---|---|---|---|
| 4,229,365 | 10/1980 | Oeser et al. | 568/937 |
| 4,287,374 | 9/1981 | North | 568/933 |
| 4,418,229 | 11/1983 | White | 568/937 |

OTHER PUBLICATIONS

Morgan et al., Tetrahedron Letters, 1978, 4837.
Finger et al., J. A. C. S., 78, 6036 (1956).

*Primary Examiner*—John F. Terapane
*Assistant Examiner*—Anne Brookes
*Attorney, Agent, or Firm*—Keil & Weinkauf

[57] ABSTRACT

Fluorine-substituted aromatic compounds are obtained by reacting the corresponding nitro compound with a salt of hydrofluoric acid in the presence of an acid halide.

5 Claims, No Drawings

PREPARATION OF FLUORINE-SUBSTITUTED AROMATIC COMPOUNDS

The introduction of fluorine atoms into aromatic compounds is one of the difficult operations in organic chemistry. The conventional methods, for example introduction via a diazonium compound by the Balz-Schiemann method, are unsatisfactory from the point of view of industrial application.

One of the methods used to date, ie. replacement of the nitro group by fluorine with the aid of salts of hydrofluoric acid, eg. potassium fluoride, gives an unsatisfactory yield (cf. Morgan et al., *Tetrahedron Lett.* 1978, 4837, and Finger et al., *J. Amer. Chem. Soc.* 78 (1956), 6034).

We have found that the replacement of the aromatically bonded nitro group by fluorine, ie. the preparation of fluorine-substituted aromatic compounds by reaction of the corresponding nitro compound with a salt of hydrofluoric acid takes place with good yield in the presence of an acid halide.

As a rule, the conversion and the yield are improved in all reactions, for example in those described by Finger et al. Nitro compounds which contain an activated nitro group are particularly advantageous. For example, halonitrobenzenes, m-dinitrobenzenes and, in particular, trinitrobenzenes are suitable for the process. In the case of the trinitrobenzenes, one or two nitro groups can be replaced by fluorine. Pseudoaromatic compounds, eg. nitropyridines, can also be converted.

Particularly suitable salts of hydrofluoric acid are the alkali metal salts, potassium fluoride being preferred for economic reasons.

For economic reasons, preferred acid halides are the acid chlorides. For example, aromatic carboxylic acid halides, such as phthaloyl chloride, can be used, but, because the reaction temperature generally required is about 150°–250° C., aliphatic carboxylic acid halides are less suitable. On the other hand, when suitable apparatuses are available, it is also possible to use, for example, phosgene, thionyl chloride or oxalyl chloride. In these cases, the procedure is advantageously carried out under superatmospheric pressure.

In order that the reactants are sufficiently soluble, the reaction should be carried out in a polar aprotic solvent which may be high boiling. Examples of suitable substances are hexamethylphosphorotriamide, dimethylformamide, N-methylpyrrolidone or, in particular, sulfolane. Where a reaction space is available to permit the procedure to be carried out under superatmospheric pressure, it is also possible to use a lower boiling solvent. In some cases, the product itself is a suitable solvent.

In deciding the amounts of reactants, it should be borne in mind that probably the halogen atom of the acid is exchanged for fluorine before the nitro group is exchanged for fluorine, and the nitro group which leaves, in the form of a nitrite ion, reacts with a fluorine atom bonded as an acid halide, nitrosyl fluoride being formed. Accordingly, 2 equivalents of fluoride and 2 equivalents of acid halide should be available per equivalent of nitro groups to be converted. The use of an excess of one or other of the reactants depends on economic considerations.

The above discussion is of a purely theoretical nature and is not intended to restrict the invention in any way.

EXAMPLE 1

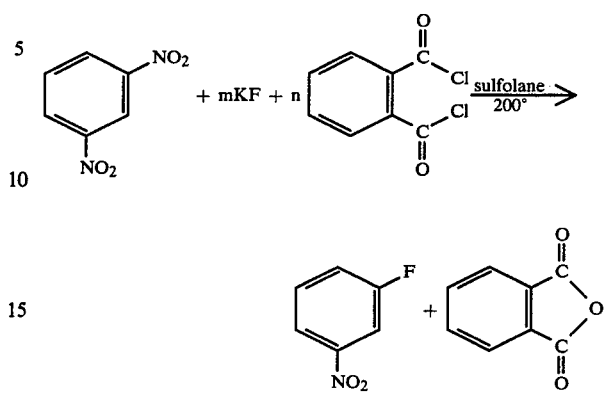

32.50 g (193.45 millimoles) of 1,3-dinitrobenzene (1,3-DNB)
56.10 g (967.2 millimoles) of KF
57.6 g (283.34 millimoles) of phthaloyl chloride (PC)
200 ml of sulfolane.

Reaction procedure 32.50 g of 1,3-DNB, 56.10 g of KF and 39.27 g of PC together in 200 ml of sulfolane are heated to 200° C. After 24 hours, 10 ml of PC are added at 140° C., and the mixture is stirred for 15 minutes at this temperature and then heated once again to 200° C. A further 3 ml of PC are added after 46 hours at 140° C., and the mixture is stirred at this temperature for 15 minutes and then heated to 200° C.

The reaction mixture is distilled under reduced pressure (oil pump).

1st fraction: 15.27 g of 3-nitrofluorobenzene (pure according to gas chromatography).

2nd fraction: The distillate is taken up with ether, the solution is washed with water until it is free of solvent, and the ether extract is dried over magnesium sulfate and concentra3.82 g of pure 3-nitrofluorobenzene are obtained. Total yield (135 millimoles) 70%, based on dinitrobenzene.

3rd fraction: The third fraction consists of sulfolane and phthalic anhydride. The latter is precipitated with dilute hydrochloric acid, filtered off under suction, washed with water and dried. Yield: 30.0 g (78%) of phthalic anhydride.

EXAMPLE 2

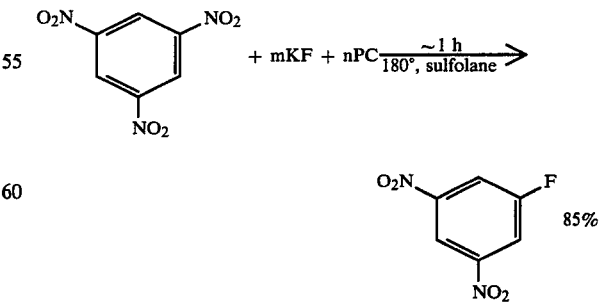

6.18 g (29.01 millimoles) of 1,3,5-trinitrobenzene
8.41 g (145.07 millimoles) of KF
5.89 g (29.01 millimoles) of phthaloyl chloride 19.50 ml of sulfolane.

Duration of reaction:

53 minutes.

Working up procedure:

The reaction mixture is diluted with water and taken up with ether, the solution is washed with water and dried over magnesium sulfate, and the ether is then removed in a thin-film evaporator. The residue is dissolved in methylene chloride and chromatographed over silica gel.

Yield:

4.85 g (85.0%) of 3,5-dinitrofluorobenzene. Melting point: 43° C., corresponding to the known value (43.8° C.; Bye, *J. Chem. Soc.* 1954, 3091).

EXAMPLE 3

Mixture:

15.00 g (70.04 millimoles) of 1,3,5-trinitrobenzene 28.59 g (493.95 millimoles) of KF 38.59 g (140.84 millimoles) of phthaloyl chloride 47.00 ml of sulfolane.

Duration of reaction:

12 hours; yield after distillation: 7.84 g (70%) of 3,5-difluoronitrobenzene.

EXAMPLE 4

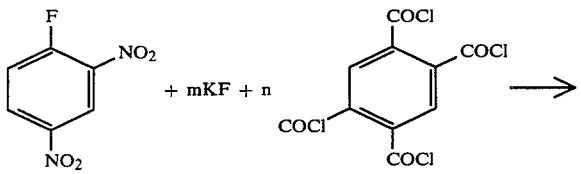

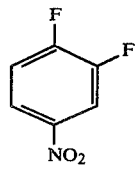

Mixture:

1.80 g (9.68 millimoles) of 2,4-dinitrofluorobenzene 3.15 g (9.66 millimoles) of pyromellitic acid tetrachloride 3.37 g (59.10 millimoles) of KF 13 ml of sulfolane.

The procedure is carried out as described above (200° C., 4 hours).

Yield:

3,4-Difluoronitrobenzene: 58%.

unreacted 2,4-dinitrofluorobenzene: 11%.

We claim:

1. A process for the production of aromatic compounds substituted by fluorine and at least one nitro group, wherein at least one fluorine atom is introduced into an aromatic compound substituted at least twice by nitro groups, said fluorine atom or atoms replacing corresponding nitro group(s), at least one nitro substituent remaining, which process comprises: reacting an aromatic compound containing at least two nitro groups and an alkali salt of hydrofluoric acid in the presence of an acid halide selected from the group consisting of carboxylic acid halide, phosgene, thionyl chloride and oxalyl chloride.

2. A process as set forth in claim 1, wherein the reaction is carried out in the presence of a carboxylic acid halide.

3. A process as set forth in claim 2, wherein the reaction is carried out in the presence of phthaloyl chloride.

4. A process as set forth in claim 1, wherein the reaction is carried out in a polar aprotic solvent.

5. The process of claim 1, wherein the aromatic compound substituted at least twice by nitro groups is selected from the group consisting of m-dinitrobenzene, trinitrobenzene and halo-substituted dinitrobenzenes and trinitrobenzenes.

* * * * *